United States Patent [19]

Kalk et al.

[11] Patent Number: 4,695,632
[45] Date of Patent: Sep. 22, 1987

[54] QUATERNARY REACTIVE COMPOUNDS

[75] Inventors: Walter Kalk; Karl H. Schündehütte; Manfred Söll, all of Leverkusen, Fed. Rep. of Germany

[73] Assignee: Bayer Aktiengesellschaft, Leverkusen, Fed. Rep. of Germany

[21] Appl. No.: 14,565

[22] Filed: Feb. 23, 1979

Related U.S. Application Data

[63] Continuation of Ser. No. 804,858, Jun. 8, 1977, abandoned.

[30] Foreign Application Priority Data

Jun. 12, 1976 [DE] Fed. Rep. of Germany ..... 26264959

[51] Int. Cl.$^4$ .................. C07D 251/46; C07D 251/52; C07D 251/18; C07D 401/12
[52] U.S. Cl. .................... 544/194; 544/208; 544/113; 544/205; 544/206; 544/207; 544/204; 544/209; 544/211; 544/212; 544/210; 544/213; 544/83
[58] Field of Search ............. 544/194, 208, 113, 205, 544/206, 207, 204, 209, 211, 212, 210, 213, 83

[56] References Cited

U.S. PATENT DOCUMENTS

| | | | |
|---|---|---|---|
| 2,719,156 | 9/1955 | De Benneville et al. | 544/113 |
| 3,278,253 | 10/1966 | Weckler et al. | 544/194 |
| 3,732,218 | 4/1973 | Gerd et al. | 544/208 |
| 3,732,220 | 5/1973 | O'Brien et al. | 544/113 |
| 4,171,955 | 10/1979 | Perrin et al. | 544/208 |
| 4,180,664 | 12/1979 | Perrin et al. | 544/208 |

FOREIGN PATENT DOCUMENTS 1094699 12/1960 Fed. Rep. of Germany ...... 544/211

Primary Examiner—John M. Ford
Attorney, Agent, or Firm—Sprung Horn Kramer & Woods

[57] ABSTRACT

Quaternary compounds of the formula

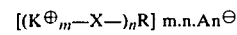

$$[(K^{\oplus}{}_m-X-)_n R] \; m.n.An^{\ominus}$$

wherein
$K^{\oplus}$ denotes a cationic organic radical,
X denotes a linking member,
R denotes the radical of a heterocyclic reactive group,
m denotes the numbers 1 or 2,
n denotes the numbers 1 or 2 and
$An^{\ominus}$ denotes an anion, can be used for increasing the affinity of anionic dyestuffs for natural or synthetic fiber materials containing nitrogen or hydroxyl groups.

10 Claims, No Drawings

QUATERNARY REACTIVE COMPOUNDS

This is a continuation of application Ser. No. 804,858, filed June 8, 1977, now abandoned.

The present invention relates to quaternary compounds of the formula $$[(K^{\oplus}{}_m-X-)_n R]\, m.n.An^{\ominus} \tag{I}$$

wherein
K⊕ denotes a cationic organic radical,
X denotes a linking member,
R denotes the radical of a heterocyclic reactive group,
m denotes the numbers of 1 or 2,
n denotes the numbers 1 or 2 and
An⊖ denotes an anion,
and their use for increasing the affinity of anionic dyestuffs for natural or synthetic fibre materials containing nitrogen or hydroxyl groups.

Examples of cationic organic radicals which may be mentioned are: quaternary ammonium and hydrazinium groups, the nitrogen atom of which can also be part of a heterocyclic structure, and sulphonium groups, isothiuronium groups, etherified hydroxylammonium groups and phosphonium groups.

Amongst these groups, those of the formula a–g are to be mentioned in particular.

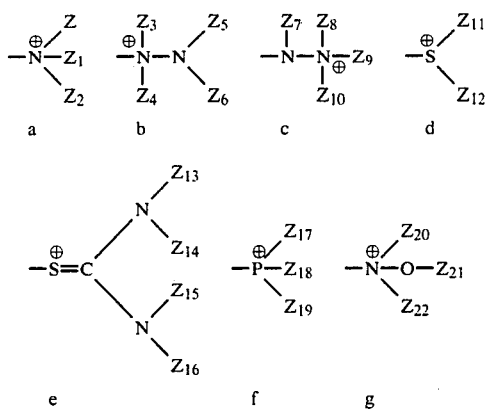

In the formula a–g, the radicals Z represent an optionally substituted alkyl, cycloalkyl, aryl, aralkyl or heterocyclic radical.

The alkyl radicals have, in particular, 1–4 carbon atoms. Amongst the cyclic radicals, those to be singled out are the cyclopentyl, cyclohexyl, phenyl, naphthyl, benzyl, phenylethyl and pyridine radicals.

The radicals can carry 1–3 substituents, such as fluorine, chlorine, bromine, $C_1$–$C_4$-alkoxy, cyano and hydroxyl, and the cyclic radicals can additionally be substituted by $C_1$–$C_4$ groups.

In addition, 2 or 3 of the radicals Z, conjointly with the hetero-atom to which they are bonded, can form a heterocyclic structure with, preferably, 5 or 6 ring members. For example, the radicals Z and $Z_1$, or $Z_3$ and $Z_4$, or $Z_5$ and $Z_6$, or $Z_8$ and $Z_9$ can form a pyrrolidine, piperidine, morpholine or piperazine ring and the radicals Z, $Z_1$ and $Z_2$, or $Z_8$, $Z_9$ and $Z_{10}$, can form a pyridine ring. Furthermore, the radicals $Z_5$ and $Z_7$ can also represent acyl, especially acetyl, propionyl or benzoyl.

A linking member X is understood, in particular, as an alkylene, arylene or heterocyclic radical, an alkyleneamino or aryleneamino radical, or a heterocyclic radical substituted by an amino group, or an alkyleneoxy radical, an aryleneoxy radical or a heterocyclic radical substituted by an oxy group, or an alkylenemercapto or arylenemercapto radical or a heterocyclic radical substituted by a mercapto group. The linking member X is bonded to a carbon atom of a heterocyclic ring of R. When the linking members carry an amino, oxy or mercapto group, they are bonded to R via this hetero-atom.

The abovementioned preferred definitions for alkyl, cycloalkyl, aryl and aralkyl radicals also apply when these substituents are mentioned in the text which follows.

Within the scope of this invention, halogen denotes in particular fluorine, chlorine or bromine.

According to the invention, a heterocyclic reactive group R is understood as those groups which contain at least one removable substituent bonded to a heterocyclic radical. Those which contain at least one reactive substituent bonded to a 5-membered or 6-membered heterocyclic ring, such as to a monazine, diazine or triazine ring, for example a pyridine, pyrimidine, pyridazine, pyrazine, thiazine or oxazine ring or an asymmetrical or symmetrical triazine ring, or to a ring system of this type which contains one or more fused aromatic rings, such as a quinoline, phthalazine, cinnoline, quinazoline, quinoxaline, acridine, phenazine and phenanthridine ring system are preferred; the 5-membered or 6-membered heterocyclic rings which contain at least one reactive substituent are, accordingly, preferably those which contain one or more nitrogen atoms and can contain fused 5-membered or, preferably, 6-membered carbocyclic rings.

Examples to be mentioned amongst the reactive substituents on the heterocyclic structure are halogen (Cl, Br or F), ammonium, including hydrazinium, sulphonium, sulphonyl, azido-($N_3$), ether, thiocyanato, thio, thioether, sulphinic acid and sulphonic acid.

Examples to be mentioned individually are monohalogeno- or dihalogeno-symmetrical-triazinyl radicals, for example 2,4-dichlorotriazinyl-6-, 2-amino-4-chlorotriazinyl-6-, 2-alkylamino-4-chlorotriazinyl-6-, such as 2-methylamino-4-chlorotrianzinyl-6-, 2-ethylamino-4-chlorotriazinyl-6- or 2-propylamino-4-chlorotriazinyl-6-, 2-β-oxethylamino-4-chlorotriazinyl-6-, 2-di-β-oxethylamino-4-chlorotriazinyl-6- and the corresponding sulphuric acid half-esters, 2-diethylamino-4-chlorotriazinyl-6-, 2-morpholino- or 2-piperidino-4-chlorotriazinyl-6-, 2-cyclohexylamino-4-chlorotriazinyl-6-, 2-aryl-amino-4-chlorotriazinyl-6- and substituted arylamino-4-chlorotriazinyl-6-, such as 2-phenylamino-4-chlorotriazinyl-6-, 2-(o-, m- or p-carboxy or sulphophenyl)-amino-4-chlorotriazinyl-6-, 2-alkoxy-4-chlorotriazinyl-6-, such as 2-methoxy- or ethoxy-4-chlorotriazinyl-6-, 2-(phenylsulphonylmethoxy)-4-chlorotriazinyl-6-, 2-aryloxy-4-chlorotriazinyl-6- and substituted aryloxy-4-chlorotriazinyl-6-, such as 2-phenoxy-4-chlorotriazinyl-6-, 2-(p-sulphophenyl)-oxy-4-chlorotriazinyl-6-, 2-(o-, m- or p-methyl- or methoxy-phenyl)-oxy-4-chlorotriazinyl-6-, 2-alkylmercapto- or 2-arylmercapto- or 2-(substituted aryl)-mercapto-4-chlorotriazinyl-6-, such as 2-β-hydroxyethyl-mercapto-4-chlorotriazinyl-6-, 2-phenylmercapto-4-chlorotriazinyl-6-, 2-(4'-methylphenyl)-mercapto-4-chlorotriazinyl-6- and 2-(2',4'-dinitro)-phenylmercapto-4-chlorotriazinyl-6-, 2-methyl-4-chlorotriazinyl-6-, 2-phenyl-4-chlorotriazinyl-6-, mono-, di- or trihalogenopyrimidinyl radicals, such as 2,4-dichloropyrimidinyl-6-, 2,4,5-trichloropyrimidinyl-6- and 2,4-dichloro-5-nitro- or -5-methyl or -5-carboxymethyl- or -5-carboxy- or -5-cyano- or -5-vinyl- or -5-vinyl- or 5-sulpho- or -5-mono-, -di- or -trichloromethyl- or -5-carboalkoxy-pyrimidinyl-6-, as well as the corresponding bromine and fluorine derivatives of the above-mentioned chlorine-substituted heterocyclic radicals and amongst the latter, for example, 2-fluoro-4-pyrimidinyl-, 2,6-difluoro-4-pyrimidinyl-, 2,6-difluoro-5-chloro-4-pyrimidinyl-, 2-fluoro-5,6-dichloro-4-pyrimidinyl-, 2,6-difluoro-5-methyl-4-pyrimidinyl-, 2,5-difluoro-6-methyl-4-pyrimidinyl-, 2-fluoro-5-methyl-6-chloro-4-pyrimidinyl-, 2-fluoro-5-nitro-6-chloro-4-pyrimidinyl-, 5-bromo-2-fluoro-4-pyrimidinyl-, 2-fluoro-5-cyano-4-pyrimidinyl-, 2-fluoro-5-methyl-4-pyrimidinyl-, 2,5,6-trifluoro-4-pyrimidinyl-, 5-chloro-6-chloromethyl-2-fluoro-4-pyrimidinyl-, 2,6-difluoro-5-bromo-4-pyrimidinyl-, 2-fluoro-5-bromo-6-methyl-4-pyrimidinyl-, 2-fluoro-5-bromo-6-chloromethyl-4-pyrimidinyl-, 2,6-difluoro-5-chloromethyl-4-pyrimidinyl-, 2,6-difluoro-5-nitro-4-pyrimidinyl-, 2-fluoro-6-methyl-4-pyrimidinyl-, 2-fluoro-5-chloro-6-methyl-4-pyrimidinyl-, 2-fluoro-5-chloro-4-pyrimidinyl-, 2-fluoro-6-chloro-4-pyrimidinyl-, 6-trifluoromethyl-5-chloro-2-fluoro-4-pyrimidinyl-, 6-trifluoromethyl-2-fluoro-4-pyrimidinyl-, 2-fluoro-5-nitro-4-pyrimidinyl-, 2-fluoro-5-trifluoromethyl-4-pyrimidinyl-, 2-fluoro-5-phenyl- or -5-methyl-sulphonyl-4-pyrimidinyl-, 2-fluoro-5-carbonamido-4-pyrimidinyl-, 2-fluoro-5-carbomethoxy-4-pyrimidinyl-, 2-fluoro-5-bromo-6-trifluoromethyl-4-pyrimidinyl-, 2-fluoro-6-carbonamido-4-pyrimidinyl-, 2-fluoro-6-carbomethoxy-4-pyrimidinyl-, 2-fluoro-6-phenyl-4-pyrimidinyl-, 2-fluoro-6-cyano-4-pyrimidinyl-, 2,6-difluoro-5-methylsulphonyl-4-pyrimidinyl-, 2-fluoro-5-sulphonamido-4-sulphonamido-4-pyrimidinyl-, 2-fluoro-5-chloro-6-carbomethoxy-4-pyrimidinyl- and 2,6-difluoro-5-trifluoromethyl-4-pyrimidinyl-; triazine radicals containing sulphonyl groups, such as 2,4-bis-(phenylsulphonyl)-triazinyl-6-, 2-(3'-carboxyphenyl)-sulphonyl-4-chlorotriazinyl-6-, 2-(3'-sulphophenyl-sulphonyl)-4-clorotriazinyl-6- and 2,4-bis-(3'-carboxy-phenylsulphonyl)-triazinyl-6-; and pyrimidine rings containing sulphonyl groups, such as 2-carboxymethylsulphonyl-pyrimidinyl-4-, 2-methylsulphonyl-6-methyl-pyrimidinyl-4-, 2-methylsulphonyl-6-ethyl-pyrimidinyl-4-, 2-phenylsulphonyl-5-chloro-6-methyl-pyrimidinyl-4-, 2,6-bis-methylsulphonyl-pyrimidinyl-4-, 2,6-bis-methylsulphonyl-5-chloro-pyrimidinyl-4-, 2,4-bis-methylsulphonyl-pyrimidine-5-sulphonyl, 2-methylsulphonyl-pyrimidinyl-4-, 2-phenylsulphonylpyrimidinyl-4-, 2-trichloromethylsulphonyl-6-methyl-pyrimidinyl-4-, 2-methylsulphonyl-5-chloro-6-methyl-pyrimidinyl-4-, 2-methylsulphonyl-5-bromo-6-methyl-pyrimidinyl-4-, 2-methylsulphonyl-5-chloro-6-ethyl-pyrimidinyl-4-, 2-methylsulphonyl-5-chloro-6-chloromethyl-pyrimidinyl-4-, 2-methylsulphonyl-4-chloro-6-methyl-pyrimidine-5-sulphonyl-, 2-methylsulphonyl-5-nitro-6-methyl-pyrimidinyl-4-, 2,5,6-tris-methylsulphonyl-pyrimidinyl-4-, 2-methylsulphonyl-5,6-dimethyl-pyrimidinyl-4-, 2-ethylsulphonyl-5-chloro-6-methyl-pyrimidinyl-4-, 2-methylsulphonyl-6-chloro-pyrimidinyl-4-, 2,6-bis-methylsulphonyl-5-chloropyrimidinyl-4-, 2-methylsulphonyl-6-carboxy-pyrimidinyl-4-, 2-methylsulphonyl-5-sulpho-pyrimidinyl-4-, 2-methylsulphonyl-6-carbomethoxy-pyrimidinyl-4-, 2-methylsulphonyl-5-carboxypyrimidinyl-4-, 2-methylsulphonyl-5-cyano-6-methoxy-pyrimidinyl-4-, 2-methylsulphonyl-5-chloro-pyrimidinyl-4-, 2-sulphoethylsulphonyl-6-methylpyrimidinyl-4-, 2-methylsulphonyl-5-bromopyrimidinyl-4-, 2-phenylsulphonyl-5-chlor-pyrimidinyl-4- and 2-carboxymethylsulphonyl-5-chloro-6-methyl-pyrimidinyl-4-.

Possible anions An⊖ are anions of both inorganic and organic acids. Examples which may be mentioned are: chloride, bromide, sulphate, phosphate, tetrafluoborate and anions of aromatic and lower aliphatic carboxylic acids and sulphur acids, such as benzenesulphonate, p-toluenesulphonate, methanesulphonate, ethanesulphonate, methosulphate, ethosulphate or acetate.

The anion is generally determined by the process of preparation and the isolation of the products I. The anions can, however, be replaced by any other desired anions in a known manner.

Amongst the compounds of the formula I, those of the formula

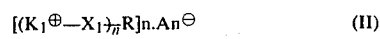

$$[(K_1^{\oplus}{-}X_1{\rightarrow_{\overline{n}}}R]_n \cdot An^{\ominus} \qquad (II)$$

wherein
$K_1^{\oplus}$ denotes an ammonium, hydrazinium, sulphonium, isothiuronium, phosphonium or etherified hydroxylammonium group and
$X_1$ denotes an alkylene or arylene radical, which is bonded directly or via N, O or S to a carbon atom of the heterocyclic ring of R,
and wherein
n, R and An⊖ have the meaning indicated in formula (I), are to be singled out.

Compounds of the formula

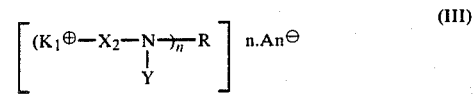

$$\left[(K_1^{\oplus}{-}X_2{-}\underset{\underset{Y}{|}}{N}{\rightarrow_{\overline{n}}}R\right] n \cdot An^{\ominus} \qquad (III)$$

wherein
$X_2$ ... alkylene or arylene,
Y ... hydrogen, alkyl or a radical of the formula

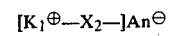

$$[K_1^{\oplus}{-}X_2{-}]An^{\ominus}$$

and
$K_1$, R, n and An⊖ have the meaning of formula (II), and wherein
the nitrogen atom is bonded to a carbon atom of the heterocyclic ring of R,
are preferred.

Amongst the compounds (III), the ammonium compounds and hydrazinium compounds are to be mentioned in particular. Amongst these, in turn, the compounds

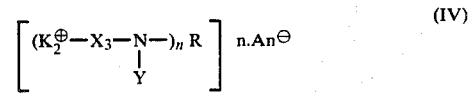

$$\left[(K_2^{\oplus}{-}X_3{-}\underset{\underset{Y}{|}}{N}{-})_n R\right] n \cdot An^{\ominus} \qquad (IV)$$

wherein
$K_2^{\oplus}$ represents a radical of the formula

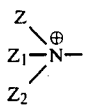

in which
Z, $Z_1$ and $Z_2$ independently of one another represent $C_1$-$C_4$-alkyl, cyclohexyl, phenyl, benzyl or phenylethyl groups, which, in turn, can be substituted by 1-3 halogen, amino, hydroxyl, $C_1$-$C_4$-alkoxy or $C_1$-$C_4$-alkyl groups, Z and $Z_1$, together with N, represent a pyrrolidine, piperidine, morpholine or piperazine radical which is optionally substituted by $C_1$-$C_4$-alkyl, or Z, $Z_1$ and $Z_2$, together with N, represent a pyridine radical which is optionally substituted by $C_1$-$C_4$-alkyl, and wherein $X_3$ represents $C_2$- or $C_3$-alkylene or o-, m- or p-phenylene and $Y_1$ represents hydrogen, $C_1$-$C_4$-alkyl or a radical of the formula

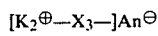

and wherein
the other symbols have the abovementioned meaning, are of particular interest.

Further preferred compounds have the formula

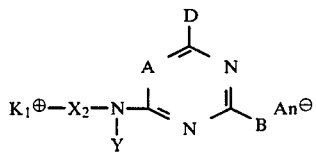

wherein
A denotes N or C-E,
E denotes hydrogen, halogen, optionally substituted alkyl, aryl, cyano, aminocarbonyl, mono- or dialkylaminocarbonyl, alkoxycarbonyl, nitro or optionally substituted alkylsulphonyl, arylsulphonyl or aralkylsulphonyl.
B denotes a reactive substituent, especially halogen or optionally substituted alkylsulphonyl, arylsulphonyl or aralkylsulphonyl,
D denotes hydrogen, halogen, optionally substituted alkyl, aryl, aralkyl, aminocarbonyl, mono- or dialkylaminocarbonyl, hydroxyl, optionally substituted alkoxy, aryloxy or aralkoxy, optionally substituted alkylsulphonyl, arylsulphonyl or aralkylsulphonyl, or a radical of the formulae

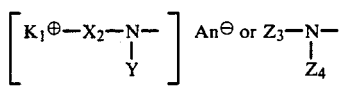

and
$Z_3$ and $Z_4$ independently of one another denote hydrogen, optionally substituted alkyl, aryl or aralkyl or,
cojointly with N, denote a 5-membered or 6-membered ring,
wherein B can also represent hydrogen when D represents halogen or optionally substituted alkylsulphonyl, arylsulphonyl or aralkylsulphonyl,
and wherein
the other symbols have the abovementioned meaning.

Moreover, compounds of the formula

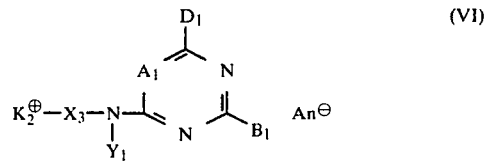

wherein
$A_1$ denotes N or C-$E_1$,
$E_1$ denotes hydrogen, halogen, methyl, ethyl, phenyl, cyano, nitro or methylsulphonyl, ethylsulphonyl or phenylsulphonyl,
$B_1$ denotes halogen, methylsulphonyl, ethylsulphonyl or phenylsulphonyl and
$D_1$ denotes hydrogen, halogen, methyl, ethyl, methylsulphonyl, ethylsulphonyl or phenylsulphonyl, trifluoromethyl, $C_1$-$C_4$-alkoxy, which is optionally substituted by halogen, cyano or hydroxyl, or a radical of the formulae

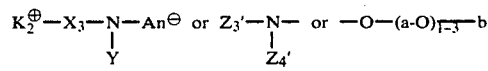

$Z_3$ and $Z_4$ independently of one another denote hydrogen, or $C_1$-$C_4$-alkyl which is optionally substituted by hydroxyl or $C_1$-$C_4$-alkoxy, or conjointly with N denote a morpholine or piperidine ring,
a denotes ethylene or propylene and
b denotes hydrogen, $C_1$-$C_4$-alkyl or phenyl,
wherein
$B_1$ can also represent hydrogen when $D_1$ represents halogen, methylsulphonyl, ethylsulphonyl or phenylsulphonyl,
and wherein
the other symbols have the abovementioned meaning, are to be mentioned.

Compounds of the formula (VI), wherein
A represents N and
$D_1$ represents the radical

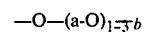

are particularly preferred.

The compounds of the formula (I) can be prepared according to methods which are in themselves known by processes 1 and 2:

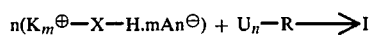

in which
U is a radical which can be split off under the reaction conditions, especially halogen.

The reaction can be carried out in aqueous or aqueous-organic solution, and preferably in a neutral or slightly acid solution, at temperatures of between 0° and 100°. The acid formed during the reaction is neutralised, for example with sodium carbonate solution. The compounds of the formula (I) are isolated from the reaction solution as solid substances or in the form of a paste. It is, however, not necessary to isolate the compounds (I) from the reaction medium. They can, for example, also be used in the form of the solutions obtained from the preparation. In order to improve the stability, buffer substances, such as phosphates, maleates or citrates, can be added to the reaction medium before, during or after the reaction.

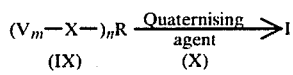

(IX)      (X)

2.

in which

V represents a substituent which can be quaternised and in particular represents an amino group.

Examples which may be mentioned of the compounds (VII) are: 1-amino-2-(trimethylammonium)-ethane chloride, 1-amino-3-(trimethylammonium)-propane chloride, 2,2'-bis-(trimethylammonium)-diethylamine dichloride, trimethyl-(3-aminophenyl)-ammonium chloride, trimethyl-(4-aminophenyl)-ammonium chloride, 1-amino-2-(pyridinium)-ethane chloride, 2,2'-bis-(pyridinium)-diethylamine dichloride, 1-amino-2-(N-methyl-morpholinium)-ethane chloride, 2,2'-bis-(N-methyl-morpholinium)-diethylamine dichloride, 1-methyl-4-(aminomethyl)-pyridinium methosulphate, trimethyl-(2-aminophenyl)-ammonium chloride, trimethyl-(2-amino-4-chloro-phenyl)-ammonium chloride, trimethyl-(3-amino-4-chloro-phenyl)-ammonium chloride, trimethyl-(2-chloro-4-amino-phenyl)-ammonium chloride, trimethyl-(2,5-dichloro-4-amino-phenyl)-ammonium chloride, trimethyl-(3,5-dichloro-4-amino-phenyl)-ammonium chloride, trimethyl-(3-amino-4-methyl-phenyl)-ammonium chloride, trimethyl-(3-methyl-4-amino-phenyl)-ammonium chloride, trimethyl-(2-methyl-3-amino-phenyl)-ammonium chloride, 1-amino-2-(N-methyl-pyrrolidinium)-ethane chloride, 1-amino-2-(N-methyl-piperidinium)-ethane chloride, 1-amino-2-(N,N'-dimethyl-piperazinium)-ethane chloride, 1-amino-2-(2'-methyl-pyridinium)-ethane chloride, 1-amino-2-(3'-methyl-pyridinium)-ethane chloride, 1-amino-2-(4'-methyl-pyridinium)-ethane chloride, 2,2'-bis-(2''-methyl-pyridinium)-diethylamine dichloride, 2,2'-bis-(3''-methyl-pyridinium)-diethylamine dichloride, 2,2'-bis-(4''-methyl-pyridinium)-diethylamine dichloride and N,N,N-trimethyl-hydrazinium methosulphate.

Suitable reactive components of the formula (VIII) are, for example, those which are based on the abovementioned reactive groups R, that is to say in general the halides, and especially the chlorides, of the said components.

Individual examples from the large number of available compounds which may be mentioned here are: trihalogeno-symmetrical-triazines, such as cyanuric chloride and cyanuric bromide, dihalogeno-monoamino-symmetrical triazines and dihalogeno-(monosubstituted amino)-symmetrical triazines, such as 2,6-dichloro-4-amino-triazine, 2,6-dichloro-4-methylaminotriazine, 2,6-dichloro-4-ethylaminotriazine, 2,6-dichloro-4-oxethylaminotriazine, 2,6-dichloro-4-phenylaminotriazine, 2,6-dichloro-4-(o-, m- or p-sulphophenyl)-aminotriazine and 2,6-dichloro-4-(2',3'-, -2',4'-, -3',4'- or -3',5'-disulphophenyl)-aminotriazine, dihalogeno-alkoxy- and -aryloxy-symmetrical-triazines, such as 2,6-dichloro-4-methoxytriazine, 2,6-dichloro-4-ethoxytriazine, 2,6-dichloro-4-isopropoxy-triazine, 2,6-dichloro-4-(2-methoxy-ethoxy)-triazine, 2,6-dichloro-4-phenoxy-triazine and 2,6-dichloro-4-(o-, m- or p-sulphophenyl)-oxytriazine, dihalogeno-alkylmercapto- and -arylmercapto-symmetrical-triazines, such as 2,6-dichloro-4-ethylmercaptotriazine, 2,6-dichloro-4-phenylmercaptotriazine and 2,6-dichloro-4-(p-methylphenyl)-mercaptotriazine; tetrahalogeno-pyrimidines, such as tetrachloro-pyrimidine, tetrabromo-pyrimidine or tetrafluoro-pyrimidine, 2,4,6-trihalogenopyrimidines, such as 2,4,6-trichloro-pyrimidine, 2,4,6-tribromopyrimidine or 2,4,6-trifluoro-pyrimidine, dihalogenopyrimidines, such as 2,4-dichloro-pyrimidine, 2,4-dibromo-pyrimidine or 2,4-difluoro-pyrimidine; 2,4,6-trichloro-5-nitro- or 5-methyl- or -5-carbomethoxy- or -5-carboethoxy- or -5-carboxymethyl- or -5-mono-, -di- or -tri-chloromethyl- or -5-carboxy- or -5-sulpho- or -5-cyano- or -5-vinyl-pyrimidine, 2,4-difluoro-6-methylpyrimidine, 2,6-difluoro-4-methyl-5-chloropyrimidine, 2,4-difluoro-pyrimidine-5-ethylsulphone, 2,6-difluoro-4-chloropyrimidine, 2,4,6-trifluoro-5-chloropyrimidine, 2,6-difluoro-4-methyl-5-bromopyrimidine, 2,4-difluoro-5,6-dichloro- or -dibromo-pyrimidine, 4,6-difluoro-2,5-dichloro- or -dibromo-pyrimidine, 2,6-difluoro-4-bromopyrimidine, 2,4,6-trifluoro-5-bromopyrimidine, 2,4,6-trifluoro-5-chloromethylpyrimidine, 2,4,6-trifluoro-5-nitropyrimidine, 2,4,6-trifluoro-5-cyanopyrimidine, 2,4,6-trifluoropyrimidine-5-carboxylic acid alkyl esters or 2,4,6-trifluoropyrimidine-5-carboxylic acid amides, 2,6-difluoro-5-methyl-4-chloropyrimidine, 2,6-difluoro-5-chloropyrimidine, 2,4,6-trifluoro-5-methylpyrimidine, 2,4,5-trifluoro-6-methylpyrimidine, 2,4-difluoro-5-nitro-6-chloropyrimidine, 2,4-difluoro-5-cyanopyrimidine, 2,4-difluoro-5-methylpyrimidine, 6-trifluoromethyl-5-chloro-2,4-difluoro-pyrimidine, 6-phenyl-2,4-difluoropyrimidine, 6-trifluoromethyl-2,4-difluoropyrimidine, 5-trifluoromethyl-2,4,6-trifluoropyrimidine, 2,4-difluoro-5-nitropyrimidine, 2,4-difluoro-5-trifluoromethyl-pyrimidine, 2,4-difluoro-5-methylsulphonyl-pyrimidine, 2,4-difluoro-5-phenyl-pyrimidine, 2,4-difluoro-5-carboxamido-pyrimidine, 2,4-difluoro-5-carbomethoxy-pyrimidine, 2,4-difluoro-6-trifluoromethyl-pyrimidine, 2,4-difluoro-5-bromo-6-trifluoromethyl-pyrimidine, 2,4-difluoro-6-carboxamido-pyrimidine, 2,4-difluoro-6-carbomethoxy-pyrimidine, 2,4-difluoro-6-phenyl-pyrimidine, 2,4-difluoro-6-cyano-pyrimidine, 2,4,6-trifluoro-5-methylsulphonyl-pyrimidine, 2,4-difluoro-5-sulphoamido-pyrimidine, 2,4-difluoro-5-chloro-6-carbomethoxy-pyrimidine, 5-trifluoromethyl-2,4-difluoropyrimidine and pyrimidine reactive components containing sulphonyl groups which can be split off, such as 2-carboxymethylsulphonyl-4-chloropyrimidine, 2-methylsulphonyl-4-chloro-6-methylpyrimidine, 2,4-bis-methylsulphonyl-6-methylpyrimidine, 2,4-bis-phenylsulphonyl-5-chloro-6-methylpyrimidine, 2,4,6-tris-methylsulphonylpyrimidine, 2,6-bismethylsulphonyl-4,5-dichloropyrimidine, 2-methylsulphonyl-4-chloropyrimidine, 2-phenylsulphonyl-4-chloropyrimidine, 2,4-bis-trichloromethylsulphonyl-6-methylpyrimidine, 2,4-bis-methylsulphonyl-5-chloro-6-methylpyrimidine, 2,4-bis-methylsulphonyl-5-bromo-6-methylpyrimidine, 2-methylsulphonyl-4,5-dichloro-6-methylpyrimidine, 2-methylsulphonyl-4,5-dichloro-6-chloromethylpyrimidine, 2-methylsulphonyl-4-chloro-5-nitro-6-methylpyrimidine, 2,4,5,6-tetramethylsulphonyl-pyrimidine, 2-methylsulphonyl-4- chloro-5,6-dimethylpyrimidine, 2-ethylsulphonyl-4,5-dichloro-6-methylpyrimidine, 2-methylsulphonyl-4,6-dichloropyrimidine, 2,4,6-tris-methylsulphonyl-5-chloropyrimidine, 2-methylsulphonyl-4-chloro-6-carboxypyrimidine, 2-methylsulphonyl-4-chloro-6-carbomethoxypyrimidine, 2-methylsulphonyl-4-chloro-5-cyano-6-methoxypyrimidine, 2-methylsulphonyl-4,5-dichloropyrimidine, 4,6-bis-methylsulphonylpyrimidine, 4-methylsulphonyl-6-chloropyrimidine, 2-sulphoethylsulphonyl-4-chloro-6-methylpyrimidine, 2-methylsulphonyl-4-chloro-5-bromopyrimidine, 2-methylsulphonyl-4-chloro-5-bromo-6-methylpyrimidine, 2,4-bis-methylsulphonyl-5-chloropyrimidine, 2-phenylsulphonyl-4,5-dichloropyrimidine, 2-phenylsulphonyl-4,5-dichloro-6-methylpyrimidine, 2-carboxymethylsulphonyl-4,5-dichloro-6-methylpyrimidine, 2-(2'- or 3'- or 4'-carboxyphenylsulphonyl)-4,5-dichloro-6-methylpyrimidine and 2,4-bis-(2'- or 3'- or 4'-carboxyphenylsulphonyl)-5-chloro-6-methylpyrimidine; examples of further reactive components of the heterocyclic series which have reactive sulphonyl substituents are 3,6-bis-phenylsulphonyl-pyridazine, 3-methylsulphonyl-6-chloropyridazine, 3,6-bis-trichloromethylsulphonyl-pyridazine, 3,6-bis-methylsulphonyl-4-methylpyridazine, 2,5,6-tris-methylsulphonylpyrazine, 2,4-bis-methylsulphonyl-1,3,5-triazine, 2,4-bis-methylsulphonyl-6-(3'-sulphophenylamino)-1,3,5-triazine, 2,4-bis-methylsulphonyl-6-N-methylanilino-1,3,5-triazine, 2,4-bis-methylsulphonyl-6-phenoxy-1,3,5-triazine, 2,4-bis-methylsulphonyl-6-trichloroethoxy-1,3,5-triazine, 2,4,6-tris-phenylsulphonyl-1,3,5-triazine, 2,4-bis-methylsulphonylquinazoline, 2,4-bis-trichloromethylsulphonylquinoline, 2,4-bis-carboxymethylsulphonylquinoline and 1-(4'-chlorocarbonylphenyl- or 2'-chlorocarbonylethyl)-4,5-bis-methylsulphonyl-pyridazone(6).

Examples of (IX) are compounds in which the said reactive groups are substituted by a non-quaternised radical, on which the compounds (VII) are based.

A quaternising agent (X) is understood as an agent which converts the radical V into $K^\oplus$ and at the same time forms the anion $An^\ominus$. Examples which may be mentioned are: alkyl halides, aralkyl halides, cycloalkyl halides, dialkyl sulphates, alkyl esters of arylsulphonic acids and also other esters of strong mineral acids and organic sulphonic acids with alcohols, preferably lower alcohols. In the presence of acids it is also possible to use acrylic acid and its derivatives and epoxides as alkylating agents. The quaternising agents can be further substituted. Examples are: dimethyl sulphate, diethyl sulphate, methyl chloride, methyl bromide, methyl iodide, methyl sulphate, ethyl bromide, n-propyl bromide, n-butyl bromide, allyl chloride, chloroacetic acid methyl ester and bromoacetic acid methyl ester, methanesulphonic acid methyl ester and methanesulphonic acid ethyl ester, ethylenechlorohydrin, chloroacetonitrile, benzyl chloride, phenylethyl chloride, phenoxy-$\beta$-chloroethyl, butenyl chloride, chloramine, O-methylsulphonylhydroxylamine, O-mesitylenesulphonylhydroxylamine, N,N-dimethylchloramine, hydroxylamine-O-sulphonic acid, acrylonitrile, ethylene oxide and propylene oxide.

The compounds of the formula (I) which are to be used according to the invention can be applied by a pre-treatment process to the fibre material to be dyed; alternatively, they are used in a single bath together with the anionic dyestuffs. They can also be applied to finished dyeings and prints by an after-treatment process. In the case of a pre-treatment, the fibre material treated with the compounds of the formula (I) is subsequently dyed from a long liquor in the manner customary for the particular dyestuffs. However, it is also possible to dye the material from a short liquor. A pre-treatment is carried out by impregnating or printing the material with aqueous padding liquors or printing pastes which contains the alkali, for example sodium bicarbonate, sodium hydroxide or, preferably, sodium carbonate, necessary for the chemical reaction with the fibre material, in addition to the compounds (I) in amounts of 20–150 g, and preferably 40–100 g, per liter of padding liquor or printing paste. The fibre material impregnated in this way is squeezed off to a liquor pick-up of 60–100% and preferably of 70–90% of the fibre weight and subjected to a heat treatment, with or without intermediate drying; this heat treatment can be effected by brief steaming, for example a steam treatment of 3 to 10 minutes at 102° to 120° C., or by brief dry heat treatment, for example 2 to 10 minutes at 120° to 150° C.; during this heat treatment, the reaction of the compounds (I) with the fibre material takes place with the formation of a chemical bond. The reaction with the fibre material can, however, also be carried out by a cold pad-batch method by rolling up the material which has been impregnated and squeezed off and keeping it at room temperature for 4 to 24 hours or at ambient temperature. In this case, care must be taken, by winding material which is impermeable to water around the fibre material, that no water can evaporate.

The residence time can be shortened to one to four hours by raising the batch temperature from room temperature to 60°–80° C.

When the compounds (I) are applied together with the dyestuffs from a single bath, padding liquors or printing pastes which contains anionic dyestuffs and also the padding auxiliaries and wetting agents customary in dyeing, the thickeners and reducing agents customary in textile printing and the necessary alkaline agents, for example sodium bicarbonate, sodium carbonate or sodium hydroxide, in addition to the compounds (I) in amounts of 20–150 g, and preferably 40–100 g, per liter of padding liquor or per kg of printing paste are prepared. Subsequent fixing is carried out in the customary manner by means of a steam, dry heat or cold pad-batch treatment.

In the case of the after-treatment of finished dyeings or prints, padding liquors which also contain the padding auxiliaries and wetting agents customary in dyeing, as well as the necessary alkaline agent, for example sodium bicarbonate, sodium carbonate or sodium hydroxide, in addition to the compounds of the composition (I) in amounts of 20–150 g, and preferably 40–100 g, per liter of padding liquor are prepared. In this case also subsequent fixing can be affected by means of a steam, dry heat or cold pad-batch treatment.

A surprisingly great improvement in the colour fastness properties and in particular in the fastness to water, perspiration and washing, compared with the colour fastness properties of conventional dyeings and prints with anionic dyestuffs, is achieved with the aid of the compounds (I) according to the invention. In addition, deeper dyeings and prints are obtained since after-treatment by rinsing and soaping does not lead to any loosening of the dyestuffs from the fibre material, as is otherwise the case with untreated dyeings and prints.

The compounds (I) are used on textile material consisting of natural cellulose, such as cotton or linen, or regenerated cellulose, such as rayon staple, rayon or high modulus fibres; these fibre materials can be present both on their own and as mixtures with synthetic fibre materials, for example those made of polyester, polyamide or polyacrylonitrile, Compounds of the composition (I) can be used for the pre-treatment, single bath treatment and after-treatment of dyeings and prints with those dyestuffs which, for example, are listed as direct dyestuffs on page 2005 to 2478 of the Colour Index, 3rd edition (1971), volume 2 and as acid dyestuffs on pages 1001–1562 of the said publication.

Compared with the known cationic after-treatment agents for direct dyestuffs, the compounds of the composition (I) have advantages in that the colour fastness properties of the dyeings pre-treated, treated in a single bath or after-treated with these compounds show a considerable improvement in respect of the fastness to washing, even at elevated washing temperatures, for example at 60° C. and in some cases even at 95° C.

(1) Synthesis of the compounds of the formula (VII)

Example 1

1-Amino-2-(trimethylammonium)-ethane chloride

Gaseous trimethylamine is passed into a solution of 174 g (1.5 mols) of 2-chloroethylamine hydrochloride in 2,500 ml of methanol for 4 hours at the boiling point. The bulk of the methanol is distilled off and the reaction product is precipitated by adding isopropanol. After drying in vacuo at 50°, 189 g (91% of theory) of a compound which has a melting point of 247°–49° and has the following formula $$H_3C-\overset{CH_3}{\underset{CH_3}{\overset{|}{\underset{|}{N^{\oplus}}}}}-CH_2-CH_2-NH_2.HCl \quad Cl^{\ominus}$$

is obtained.

Water can also be used in place of methanol as the solvent. The product was characterised by the NMR spectrum. The compound is known from German Offenlegungsschrift (German Published Specification) No. 2,128,905.

Example 2

1-Amino-3-(trimethylammonium)-propane chloride (a) Gaseous trimethylamine is passed into a solution of 130 g (1.0 mol) of 3-chloro-propylamine hydrochloride in 500 ml of methanol for 8 hours at the boiling point. After distilling off the methanol, the residual oil is stirred with isopropanol/ether whereupon it becomes crystalline.

After drying in vacuo at 50°, 102 g (67% of theory) of a compound of the following formula $$H_3C-\overset{CH_3}{\underset{CH_3}{\overset{|}{\underset{|}{N^{\oplus}}}}}-CH_2-CH_2-CH_2-NH_2.HCl \quad Cl^{\ominus}$$

are obtained. The product was characterized by the NMR spectrum.

(b) The same compound can also be obtained in the following way:

1-Acetylamino-3-dimethylamino-propane is quaternised, in acetone, with dimethyl sulphate to give 1-acetylamino-3-trimethylammonium-propane methosulphate (yield 98% of theory, melting point: 87°–90°). 1-Amino-3-(trimethylammonium)-propane chloride is obtained by heating this quaternary salt in approximately 20% strength hydrochloric acid at the reflux temperature for 2 hours.

(c) The same compound can also be prepared by direct quaternisation of 1-amino-3-dimethylamino-propane with dimethyl sulphate in water:

19.0 ml (0.2 mol) of dimethyl sulphate are added dropwise to a solution of 20.4 g (0.2 mol) of 1-amino-3-dimethylamino-propane in 100 ml of water, at 0°–5° C., with external cooling and whilst stirring. An aqueous solution which contains the above cation and methosulphate as the anion is obtained in 70% yield.

Example 3

2,2'-Bis-(trimethylammonium)-diethylamine dichloride

Gaseous trimethylamine is passed into a boiling solution of 128.7 g (0.72 mol) of 2,2'-dichloro-diethylamine hydrochloride in 450 ml of methanol for 3 hours. The bulk of the methanol is distilled off, the reaction product is precipitated by adding isopropanol and, after drying at 50°, 168 g (90% of theory) of a compound which has a melting point of >300° and has the following formula:

$$HN\begin{array}{c}(CH_2)_2-\overset{\oplus}{N}(CH_3)_3\\ \\(CH_2)_2-\overset{\oplus}{N}(CH_3)_3\end{array} \quad 2Cl^{\ominus}.HCl$$

is obtained. The product was characterised by the NMR spectrum.

Example 4

1-Amino-2-(pyridinium)-ethane chloride

A solution of 11.6 g (0.1 mol) of 2-chloroethylamine hydrochloride in 70 ml of pyridine is heated under reflux for 1 hour. After cooling, the product which has precipitated out is filtered off and recrystallized from methanol/isopropanol. After drying, 11.7 g (86.5% of theory) of a compound which has a melting point of 200°–205° and has the following formula $$\underset{}{\bigcirc}N^{\oplus}-(CH_2)_2-NH_2 \; Cl^{\ominus}.HCl$$

is obtained. The product was characterised by the NMR spectrum. The compound has been described by S. Gabriel, Ber. 53B (1920), 1990.

Example 5

2,2'-Bis-(pyridinium)-diethylamine dichloride 28.6 g (0.16 mol) of 2,2'-dichloro-diethylamine hydrochloride in 100 ml of pyridine are heated under reflux for 2 hours. After cooling, the product which has precipitated out is filtered off and stirred in acetone. After drying, 45 g (94% of theory) of a compound which has a melting point of 163°–165° and corresponds to the following formula:

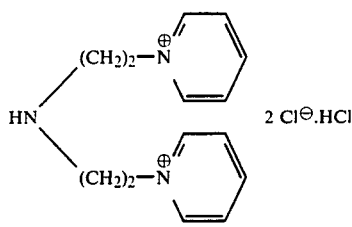

is obtained. The product was characterised by the NMR spectrum.

Example 6

1-Amino-2-(N-methyl-morpholinium)-ethane chloride 80.8 g of N-methyl-morpholine are added dropwise to a solution of 46.4 g (0.4 mol) of 2-chloroethylamine hydrochloride in 300 ml of water at room temperature, with external cooling and whilst stirring, and the mixture is then heated under reflux for 1 hour. After distilling off the solvent in vacuo, 59 g (90% of theory) of an oily compound of the following formula:

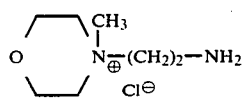

are obtained. The product was characterised by the NMR spectrum.

Example 7

2,2'-Bis-(N-methyl-morpholinium)-diethylamine dichloride 28.6 g (0.16 mol) of 2,2'-dichloro-diethylamine hydrochloride in 100 ml of N-methyl-morpholine are heated under reflux for 2 hours. After cooling to room temperature, 200 ml of acetone are added, the mixture is stirred for 1 hour and the product which has precipitated out is filtered off. After drying, 49 g (89% of theory) of a compound which has a decomposition product of 170° and has the following formula:

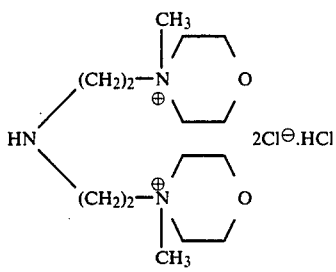

are obtained. The product was characterised by the NMR spectrum.

Example 8

1-Methyl-4-(aminomethyl)-pyridinium methosulphate 190 ml of dimethyl sulphate are added dropwise to a solution of 216 g (2.0 mols) of 4-aminomethylpyridine in 400 ml of dimethylformamide at room temperature, whilst stirring, and the mixture is then heated to 100° for 1 hour. After distilling off the solvent in vacuo, 410 g (87% of theory) of an oily compound of the following formula:

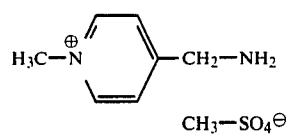

are obtained. The product was characterised by the NMR spectrum.

(2) SYNTHESIS OF THE REACTIVE SALTS OF THE FORMULA (I)

Example 9

20.7 ml (0.2 mol) of 2,4,6-trifluoro-5-chloro-pyrimidine are added dropwise, at room temperature, to 300 g of an aqueous solution which contains 0.2 mol of trimethyl-(3-aminophenyl)-ammonium chloride, whilst stirring. A pH value of 6 is maintained by gradually adding a 4N sodium carbonate solution. The reaction product precipitates out. 30 g of NaCl are added and the product is filtered off and dried in vacuo at about 30°. 55 g of a compound of the following formula:

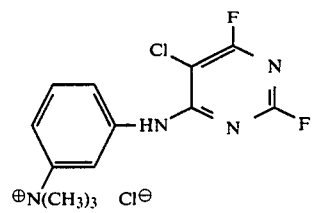

are obtained.

The compound is dissolved in water and converted into the corresponding tetrafluoborate by adding an aqueous solution of $NaBF_4$; melting point: 233°–236°.

Elementary analysis: $C_{13}H_{14}BClF_6N_4$ (386.5). Calculated: C 40.3%; H 4.0%; Cl 9.2%; N 14.5%. Found: C 40.3%; H 3.8%; Cl 9.1%; N 14.4%.

Example 10

41.4 ml (0.4 mol) of 2,4,6-trifluoro-5-chloro-pyrimidine are added dropwise, at room temperature, to a solution of 74.5 g (0.4 mol) of trimethyl-(4-aminophenyl)-ammonium chloride in 300 ml of water, whilst stirring, and a pH value of 6 is maintained using 4N sodium carbonate solution. The product gradually precipitates out. It is filtered off and dried in vacuo at 40° and 130 g of a compound of the following formula:

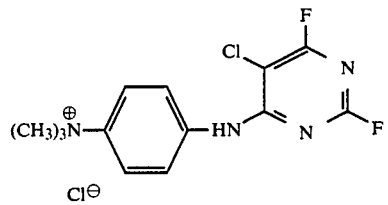

are obtained.

The compound is converted into the tetrafluoborate; melting point 234°–237°.

Elementary analysis: $C_{13}H_{14}BClF_6N_4$ (386.5). Calculated: C 40.3%; H 4.0%; Cl 9.2%; N 14.5%. Found: C 40.3%; H 3.9%; Cl 9.0%; N 14.5%.

Example 11

20.7 ml (0.2 mol) of 2,4,6-trifluoro-5-chloro-pyrimidine are added dropwise to a solution of 31.7 g (0.2 mol) of 1-amino-2-(pyridinium)-ethane chloride (see Example 4) in 100 ml of water, at room temperature and whilst stirring, and a pH value of about 6 is maintained using 4N sodium carbonate solution. After the reaction has ended, the water is distilled off in vacuo at about 30° C. 52 g of a paste which contains a compound of the following formula:

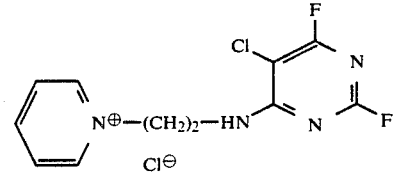

are obtained.

The corresponding tetrafluoborate was prepared as a sample for analysis; melting point 105°–109° C.

Elementary analysis: $C_{11}H_{10}BClF_6N_4$ (358.5). Calculated: C 36.8%; H 2.8%; Cl 9.9%; N 15.6%. Found: C 36.4%; H 2.8%; Cl 9.9%; N 15.6%.

Example 12

55.4 g (0.4 mol) of 1-amino-2-(trimethylammonium)-ethane chloride (see Example 1) are dissolved in 250 ml of water and 148 g (0.4 mol) of 2-methylsulphonyl-4,5-dichloro-6-methyl-pyrimidine are added in portions at room temperature, whilst stirring. The mixture is then heated to 70° and a pH value of 6 is maintained using 4N sodium carbonate solution. After the reaction has ended, the water is distilled off in vacuo and 151 g of a paste which contains a compound of the following formula

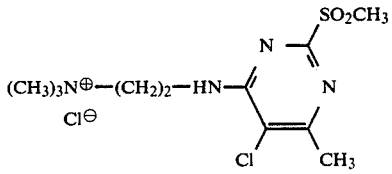

are obtained.

The corresponding tetrafluoborate was prepared as a sample for analysis; melting point: 204°–206° C.

Elementary analysis: $C_{11}H_{20}BClF_4N_4O_2S$ (394.5). Calculated: C 33.4%; H 5.1%; Cl 9.0%; N 14.2%. Found: C 33.3%; H 5.2%; Cl 9.0%; N 13.8%.

Example 13

79 g (0.2 mol) of 2-methylsulphonyl-4,5-dichloro-6-methyl-pyrimidine are added to a solution of 31.7 g (0.2 mol) of 1-amino-2-(pyridinium)-ethane chloride (see Example 4) in 200 ml of water at room temperature, whilst stirring, and the mixture is heated to 60° C.

A pH value of 6 is maintained using 4N sodium carbonate solution. After the reaction has ended, the water is distilled off in vacuo and 109 g of an oil which contains a compound of the following formula:

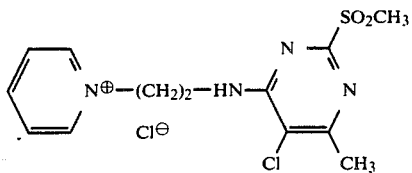

are obtained.

The corresponding tetrafluoroborate was prepared as a sample for analysis; melting point: 150°–154° C.

Elementary analysis: $C_{13}H_{16}BClF_4N_4O_2S$ (414.5). Calculated: C 37.6%; H 3.9%; Cl 8.6%; N 13.5%. Found: C 37.2%; H 3.9%; Cl 8.7%; N 13.3%.

Example 14

A solution of 72 g (0.4 mol) of 2-methoxy-4,6-dichloro-s-triazine in 300 ml of acetone is poured into 300 ml of ice water. A suspension forms end a solution of 74.5 g (0.4 mol) of trimethyl-(4-aminophenyl)-ammonium chloride in 300 ml of water is added dropwise to this. A pH value of 6 is maintained using 4N sodium carbonate solution. After the reaction has ended, the water is distilled off in vacuo at about 40°. 245 g of a paste which contains a compound of the following formula:

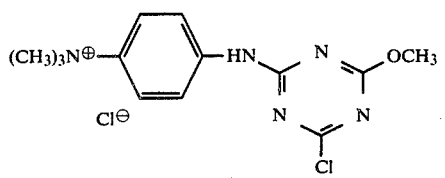

are obtained.

The corresponding tetrafluoborate was prepared as a sample for analysis; melting point: 215°–220° C.

Elementary analysis: $C_{13}H_{17}BClF_4N_5O$ (381.5). Calculated: C 41.0%; H 4.4%; N 18.3%. Found: C 41.8%; H 5.0%; N 17.9%.

The table which follows contains further examples of reactive salts of the formula I. They were prepared by a procedure analogous to that indicated in Examples 9 (for pyrimidine derivatives) and 14 (triazine derivatives).

| Example No. | Compound VII | Compound VIII | Compound I |
|---|---|---|---|
| 15 | pyridinium-(CH₂)₂-NH₂ Cl⁻ | tetrachloropyrimidine | pyridinium-(CH₂)₂-NH-(trichloropyrimidine) Cl⁻ |
| 16 | (CH₃)₃N⁺-(CH₂)₂-NH₂ Cl⁻ | " | (CH₃)₃N⁺-(CH₂)₂-NH-(trichloropyrimidine) Cl⁻ |
| 17 | 3-(trimethylammonio)aniline Cl⁻ | " | 3-(trimethylammonio)anilino-trichloropyrimidine Cl⁻ |
| 18 | " | methylsulfonyl-methyl-dichloropyrimidine | 3-(trimethylammonio)anilino-(methylsulfonyl-methyl-chloropyrimidine) Cl⁻ |
| 19 | [pyridinium-(CH₂)₂-NH]₂ Cl⁻ | tetrachloropyrimidine | [pyridinium-(CH₂)₂-NH-(dichloropyrimidine)]₂ Cl⁻ |
| 20 | " | " | bis[pyridinium-(CH₂)₂-NH-(dichloropyrimidine)]₂ Cl⁻ |

| Example No. | Compound VII | Compound VIII | Compound I |
|---|---|---|---|
| 21 | 2(CH₃)₃N⊕—C₆H₄—NH₂ Cl⊖ | " | (CH₃)₃N⊕—C₆H₄—NH—[triazine-Cl]—NH—C₆H₄—N⊕(CH₃)₃ 2Cl⊖ |
| 22 | [Pyridinium-N⊕—(CH₂)₂—NH]₂ Cl⊖ | Cl—[triazine]—OCH₃ (dichloro-methoxy-triazine) | [Pyridinium-N⊕—(CH₂)₂—NH—triazine(Cl)(OCH₃)]₂ Cl⊖ |
| 23 | Pyridinium-N⊕—(CH₂)₂—NH₂ Cl⊖ | " | Pyridinium-N⊕—(CH₂)₂—NH—triazine(Cl)(OCH₃) Cl⊖ |
| 24 | " | Cl—[triazine]—O—CH(CH₃)₂ | Pyridinium-N⊕—(CH₂)₂—NH—triazine(Cl)(O—CH(CH₃)₂) Cl⊖ |
| 25 | (CH₃)₃N⊕—(CH₂)₂—NH₂ Cl⊖ | " | (CH₃)₃N⊕—(CH₂)₂—NH—triazine(Cl)(O—CH(CH₃)₂) Cl⊖ |
| 26 | " | Cl—[triazine]—O(CH₂)₂—OCH₃ | (CH₃)₃N⊕—(CH₂)₂—NH—triazine(Cl)(O(CH₂)₂—OCH₃) Cl⊖ |

4,695,632

-continued

| Example No. | Compound VII | Compound VIII | Compound I |
|---|---|---|---|
| 27 | 4-($(CH_3)_3N^+$ $Cl^-$)-C$_6$H$_4$-NH$_2$ | " | 4-($(CH_3)_3N^+$ $Cl^-$)-C$_6$H$_4$-NH-C(=N-)(N=)(Cl)(O(CH$_2$)$_2$-OCH$_3$) triazine |
| 28 | [Pyridinium-N$^+$-(CH$_2$)$_2$-NH]$_2$ $Cl^-$ | " | [Pyridinium-N$^+$-(CH$_2$)$_2$-N(triazine-Cl, O(CH$_2$)$_2$-OCH$_3$)]$_2$ $Cl^-$ |
| 29 | " | Cl-triazine-O(CH$_2$)$_2$-O-(CH$_2$)$_2$-OC$_2$H$_5$ | [Pyridinium-N$^+$-(CH$_2$)$_2$-N(triazine-Cl, O(CH$_2$)$_2$-O-(CH$_2$)$_2$-OC$_2$H$_5$)]$_2$ $Cl^-$ |
| 30 | Pyridinium-N$^+$-(CH$_2$)$_2$-NH$_2$ $Cl^-$ | (Cl-triazine)$_2$-O(CH$_2$)$_2$-O | [Pyridinium-N$^+$-(CH$_2$)$_2$-NH-triazine-Cl]$_2$-O-CH$_2$ $Cl^-$ |
| 31 | $(CH_3)_3N^+$-(CH$_2$)$_2$-NH$_2$ $Cl^-$ | Cl-triazine-OCH$_3$ | $(CH_3)_3N^+$-(CH$_2$)$_2$-NH-triazine(Cl)(OCH$_3$) $Cl^-$ |
| 32 | $(CH_3)_3N^+$-(CH$_2$)$_3$-NH$_2$ $Cl^-$ | " | $(CH_3)_3N^+$-(CH$_2$)$_3$-NH-triazine(Cl)(N=C(CH$_3$)) $Cl^-$ |

Example 33

A dyeing of 3% of C.I. Direct Blue 151 (=C.I. No. 24,175) (Colour Index, 3rd edition (1971), volume 2) is produced on a cut piece of cotton fabric from an aqueous dye liquor using the dyeing procedure customary for these dyestuffs, rinsed and dried. This dyeing is impregnated, on a dyeing padder, at room temperature, with a solution, which contains 55 g of the compound from Example 21 and 20 g of sodium carbonate per liter, and is squeezed off so that the liquor pick-up of the dyeing is about 80%. The material is then dried in a drying cabinet at 60°–70° C. and then steamed for 8 minutes at 102° C. When the rinsing operations at room temperature and 60°–70° C., which now follow, are carried out, for 5 minutes in each case, the rinsing baths remain uncoloured and on subsquent treatment in distilled water at high temperature only slight staining of the treatment liquor takes place in the course of 20 minutes.

A blue dyeing with very good fastness to light, water, perspiration and washing was obtained.

Example 34

A cut piece of cotton fabric, which is dyed with 3% of C.I. Direct Blu 151, is impregnated, on a dyeing padder, with a solution, which contains 100 g of the compound from Example 9 and 20 g of sodium carbonate per liter, squeezed off to a liquor pick-up of about 80% and dried in a drying cabinet at 60°–70° C. The cotton fabric pre-treated in this way is then heated to 150° C. for 3 minutes. On subsequent rinsing in water at room temperature and at 60°–70° C., for 5 minutes in each case, and on treatment in boiling water for 20 minutes, no staining of the treatment liquors takes place.

The blue dyeing thus obtained is distinguished by good colour fastness properties and in particular by good fastness to water and washing.

Similar results are obtained when 104 g of the compound from Example 10, 84 g of the compound from Example 11, 106 g of the compound from Example 12 or 112 g of the compound from Example 13 are used in place of 100 g of the compound from Example 9.

Example 35

A cut piece of regenerated cellulose fabric dye with 2% of C.I. Direct Red 76 (=C.I. No. 40,270) is impregnated at room temperature with a solution, which contains 102 g of the compound from Example 24 and 20 g of sodium carbonate per liter, and squeezed off so that the liquor pick-up is about 80%. The fabric treated in this way is rolled onto a glass rod and suspended in a closed glass vessel for 24 hours at room temperature. On rinsing and after-treatment in boiling water, no staining of the treatment liquors takes place.

The scarlet dyeing which is thus obtained displays good fastness to light, water, perspiration and washing.

Similar results are obtained when 101 g of the compound from Example 26, 151 g of the compound from Example 28, 102 g of the compound from Example 14, 88 g of the compound from Example 23 or 84 g of the compound from Example 29 are employed in place of 102 g of the compound from Example 24.

We claim:

1. A compound of the formula

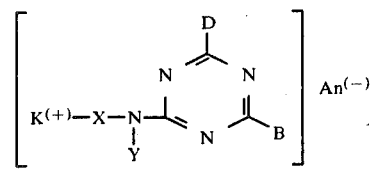

wherein
B is halogen, methylsulphonyl, ethylsulphonyl, or phenylsulphonyl; or also is hydrogen when D is halogen, methylsulphonyl, ethylsulphonyl, or phenylsulphonyl;
D is hydrogen, halogen, methyl, ethyl, methylsulphonyl, ethylsulphonyl, phenylsulphonyl, trifluoromethyl, $C_1$–$C_4$-alkoxy, halo-$C_1$–$C_4$-alkoxy, cyano-$C_1$–$C_4$-alkoxy, hydroxy-$C_1$–$C_4$-alkoxy, or a radical of the formula

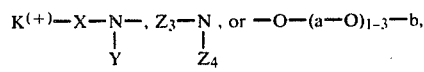

wherein
B and D are not halogen at the same time;
$Z_3$ and $Z_4$, independently of each other, are hydrogen, $C_1$–$C_4$-alkyl, hydroxy-$C_1$–$C_4$-alkyl, $C_1$–$C_4$-alkoxy-$C_1$–$C_4$-alkyl, or when joined together with N are morpholino or piperidino;
a is ethylene or propylene;
b is hydrogen, $C_1$–$C_4$-alkyl, or phenyl;

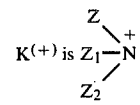

Z, $Z_1$ and $Z_2$ independently of one another are $C_1$–$C_4$-alkyl, cyclohexyl, phenyl, benzyl or phenylethyl, which are unsubstituted or substituted by 1–3 halogen, amino, hydroxy, $C_1$–$C_4$-alkoxy or $C_1$–$C_4$-alkyl;
Z and $Z_1$, together with N, are pyrrolidine, piperidine morpholine or piperazine, which is unsubstituted or substituted by $C_1$–$C_4$-alkyl; or Z, $Z_1$ and $Z_2$, together with N, are pyridine which is unsubstituted or substituted by $C_1$–$C_4$-alkyl,
X is $C_2$–$C_3$-alkylene, o-phenylene, m-phenylene, or p-phenylene;
Y is hydrogen or $C_1$–$C_4$-alkyl; and
$An^{(-)}$ is an anion.

2. A compound according to claim 1, in which X is $C_2$–$C_3$-alkylene.

3. A compound according to claim 1, in which X is o-phenylene, m-phenylene or p-phenylene, and D is

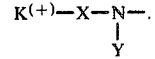

4. A compound according to claim 1, in which B is fluorine.

5. A compound according to claim 1, in which B is halogen.

6. A compound according to claim 5, in which B is chlorine or fluorine.

7. A compound according to claim 1, in which D is

8. A compound according to claim 1, of the formula
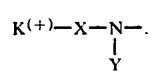
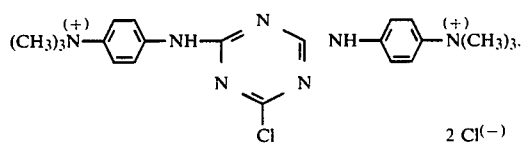
9. A compound according to claim 1, of the formula
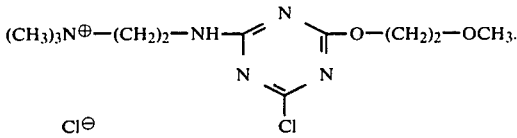
10. A compound according to claim 1, of the formula
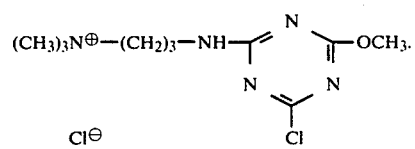
* * * * *

UNITED STATES PATENT AND TRADEMARK OFFICE
CERTIFICATE OF CORRECTION

PATENT NO. : 4,695,632
DATED : Sept. 22, 1987
INVENTOR(S) : Kalk et al.

It is certified that error appears in the above-identified patent and that said Letters Patent is hereby corrected as shown below:

| | |
|---|---|
| Col. 3, line 6 | Delete "-5- vinyl-" |
| Col. 3, line 44 | Correct spelling of --chlorotriazinyl-- |
| Col. 5, line 66 | Correct spelling of --conjointly-- |
| Col. 16, line 31 | Delete "end" and substitute --and-- |
| Col. 23, line 48 | Delete "dye" and substitute --dyed-- |

Signed and Sealed this

Thirty-first Day of May, 1988

Attest:

DONALD J. QUIGG

Attesting Officer

Commissioner of Patents and Trademarks